(12) United States Patent
Matsuoka et al.

(10) Patent No.: US 11,850,617 B2
(45) Date of Patent: Dec. 26, 2023

(54) ELECTROSTATIC ATOMIZING APPARATUS AND ELECTROSTATIC ATOMIZING METHOD

(71) Applicant: Panasonic Intellectual Property Management Co., Ltd., Osaka (JP)

(72) Inventors: Masaru Matsuoka, Osaka (JP); Takahiro Yamaguchi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1135 days.

(21) Appl. No.: 16/364,467

(22) Filed: Mar. 26, 2019

(65) Prior Publication Data

US 2019/0308207 A1 Oct. 10, 2019

Related U.S. Application Data

(60) Provisional application No. 62/653,559, filed on Apr. 6, 2018.

(51) Int. Cl.
*F24F 6/12* (2006.01)
*B05B 5/025* (2006.01)
(Continued)

(52) U.S. Cl.
CPC ............ *B05B 5/0255* (2013.01); *A61L 9/14* (2013.01); *B05B 5/035* (2013.01); *B05B 5/057* (2013.01);
(Continued)

(58) Field of Classification Search
CPC ..... B05B 5/0255; B05B 5/035; B05B 5/0533; B05B 5/057; B05B 5/03; B05B 12/004;
(Continued)

(56) References Cited

U.S. PATENT DOCUMENTS 3,306,108 A * 2/1967 Harrington ............ G01N 19/10
73/335.13
4,006,674 A * 2/1977 Culver ...................... F24F 6/02
261/DIG. 15
(Continued)

FOREIGN PATENT DOCUMENTS

JP 2005-296753 10/2005
JP 4778276 7/2011
(Continued)

OTHER PUBLICATIONS

EPO translation of JP 2013108722 (Year: 2013).*
(Continued)

*Primary Examiner* — Stephen Hobson
(74) *Attorney, Agent, or Firm* — Wenderoth, Lind & Ponack, L.L.P.

(57) ABSTRACT

An electrostatic atomizing apparatus includes an air flow path, a humidifier, and electrode section, and a control unit. The air flow path has an air intake port and an air exhaust port. The humidifier includes a portion of the air flow path and humidifies air taken in through the air intake port. The electrode section includes a portion of the air flow path and produces charged particulate water by causing water in the air humidified by the humidifier to condense on an electrode and applying voltage to the electrode. A flow rate of the air in the air flow path is regulated in accordance with at least one of humidity and temperature of the air taken in through the air intake port.

10 Claims, 10 Drawing Sheets

(51) Int. Cl.
  *B05B 5/053* (2006.01)
  *B05B 5/057* (2006.01)
  *B05B 5/035* (2006.01)
  *F24F 6/04* (2006.01)
  *A61L 9/14* (2006.01)
  *F24F 13/08* (2006.01)

(52) U.S. Cl.
  CPC .............. *B05B 5/0533* (2013.01); *F24F 6/04* (2013.01); *F24F 6/12* (2013.01); *A61L 2209/134* (2013.01); *A61L 2209/16* (2013.01); *A61L 2209/22* (2013.01); *F24F 13/08* (2013.01); *F25D 2317/0413* (2013.01)

(58) Field of Classification Search
  CPC ...... B05B 12/10; A61L 9/14; A61L 2209/134; A61L 2209/16; A61L 2209/22; F24F 6/04; F24F 6/12; F24F 13/08; F25D 2317/0413; B64D 2013/0662

See application file for complete search history.

(56) References Cited

U.S. PATENT DOCUMENTS

| | | | | |
|---|---|---|---|---|
| 4,954,802 A | * | 9/1990 | Wasserstrom | H01H 37/043 337/380 |
| 5,428,964 A | * | 7/1995 | Lobdell | G05D 27/02 340/672 |

FOREIGN PATENT DOCUMENTS

| | | | |
|---|---|---|---|
| JP | 2011-169574 | | 9/2011 |
| JP | 4877410 | | 12/2011 |
| JP | 2012-50701 | | 3/2012 |
| JP | 2013-79755 | | 5/2013 |
| JP | 2013-108722 | | 6/2013 |
| JP | 2013108722 | * | 6/2013 |
| JP | 2014074571 | * | 4/2014 |
| JP | 2015-72112 | | 4/2015 |
| JP | 2016-95115 | | 5/2016 |

OTHER PUBLICATIONS

EPO translation of JP2014074571 (Year: 2014).*
Extended European Search Report dated Aug. 26, 2019 in corresponding European Patent Application No. 19165427.6.

* cited by examiner

ELECTROSTATIC ATOMIZING APPARATUS AND ELECTROSTATIC ATOMIZING METHOD

CROSS-REFERENCE TO RELATED APPLICATION

This application claims benefit to U.S. provisional application No. 62/653,559, filed on Apr. 6, 2018. The entire disclosure of U.S. provisional application 62/653,559 is hereby incorporated herein by reference.

BACKGROUND

Technical Field

The present disclosure relates to an electrode cooling-type electrostatic atomizing technology that eliminates the need to directly supply water to a water application electrode by cooling the water application electrode and causing water vapor in the air to condense on the water application electrode.

BACKGROUND ART

Japanese Patent No. 4877410, for example, discloses electrostatically atomizing the water in the air to produce charged particulate water having a particle size of 3 to 50 nm, and reacting the charged particulate water with any of pollen antigens, molds, fungi, or viruses to inactivate the pollen antigens, molds, fungi, or viruses. With electrode cooling-type electrostatic atomizing apparatuses, it is possible to acquire the water needed for electrostatic atomization by cooling the water application electrode and causing the water vapor in the air to condense on the water application electrode.

BRIEF SUMMARY

In low humidity environments such as in aircraft flying at altitudes of 10 km, there are cases where the electrostatic atomizing apparatus described above cannot cause a sufficient amount of water to condense and, as a result, electrostatic atomization cannot be carried out.

The present disclosure provides an electrostatic atomizing apparatus and a method that are effective for maintaining the humidity needed to carry out electrostatic atomization, even in low humidity environments such as in aircraft and other moving bodies, and in facilities.

The electrostatic atomizing apparatus according to the present disclosure includes an air flow path, a humidifier, an electrode section, and a control unit. The air flow path includes an air intake port and an air exhaust port. The humidifier includes a portion of the air flow path and humidifies air taken in through the air intake port. The electrode section includes a portion of the air flow path and produces charged particulate water by causing water in the air humidified by the humidifier to condense on an electrode and applying voltage to the electrode. A flow rate of the air in the air flow path is regulated in accordance with at least one of humidity and temperature of the air taken in through the air intake port.

An electrostatic atomizing method of the present disclosure includes measuring at least one of temperature and humidity of air taken in through an air intake port, regulating a flow rate of the air taken in through the air intake port in accordance with at least one of the temperature and the humidity that are measured, humidifying the air taken in through the air intake port, producing charged particulate water by causing water in the air that is humidified to condense on an electrode and applying voltage to the electrode, and exhausting air that includes the charged particulate water through an air exhaust port.

BRIEF DESCRIPTION OF DRAWINGS

FIG. 1 illustrates the schematic configuration of an electrostatic atomizing apparatus according to the present disclosure;

FIG. 2 illustrates the configuration of an electrostatic atomizing apparatus according to Embodiment 1;

FIG. 3 illustrates the configuration of an electrostatic atomizing apparatus according to a modification example of Embodiment 1;

FIG. 4 illustrates a flowchart of air humidification by the electrostatic atomizing apparatus according to Embodiment 1;

FIG. 5 illustrates a flowchart of electrostatic atomization by the electrostatic atomizing apparatus according to Embodiment 1;

FIG. 6 illustrates an example of a configuration for executing open-close rate control based on temperature/humidity, by an electrostatic atomizing apparatus according to Embodiment 2;

FIG. 7 illustrates the configuration of an electrostatic atomizing apparatus according to Embodiment 3;

FIG. 8 illustrates a flowchart of air humidification in Embodiment 3;

FIG. 9 illustrates the configuration of an electrostatic atomizing apparatus according to another embodiment; and FIG. 10 illustrates a graph for explaining the required amount of water vapor for the electrostatic atomizing apparatus.

DETAILED DESCRIPTION

Next, embodiments of the present disclosure are described in detail while referencing the drawings. Note that, in some cases, unnecessarily detailed descriptions are foregone. For example, detailed descriptions of well-known matters and redundant descriptions of configurations and constituents that are substantially the same may be foregone.

Note that the following description and attached drawings are provided for the purpose of enabling a person skilled in the art to comprehend the present disclosure, and are not intended to limit the subject matters recited in the claims.

Note that, in the following description, unless otherwise noted, the term "humidity" means "relative humidity."

A typical aircraft takes in outside air. At high altitudes of 10 km, the ambient temperature is about −55° C. and, as such, even if that air is heated, the amount of water vapor contained therein is very small. Additionally, aircraft are used for a long period of time. Specifically, it is said that the aircraft has a life of about 30 years. Since the structures of aircraft are mainly metal, in order to prevent corrosion and fatigue failure due to repeated expansion and contraction caused by water adhesion, humidification to the humidity of 40% to 50%, at which humans feel comfortable, is not achievable.

Due to these reasons, unlike home environments, the humidity in an aircraft is extremely low, and the water necessary for the electrostatic atomizing apparatus cannot be supplied from the air. Additionally, in the unique environment of the aircraft, it is difficult to always be reachable to a water source, and weight is directly linked to fuel costs. As such, it is only possible to supply the minimum amount of water required.

To solve these problems, the present disclosure provides an electrostatic atomizing apparatus and an electrostatic atomizing method whereby humidification control can be effectively carried out and electrostatic atomization can be stably executed, even in low humidity environments.

Hereinafter, embodiments are described.

1. Embodiment 1

The following example describes a case in which charged particulate water is produced while controlling humidification by an electrostatic atomizing apparatus installed in an aircraft.

1-1 Configuration

Figure 1:
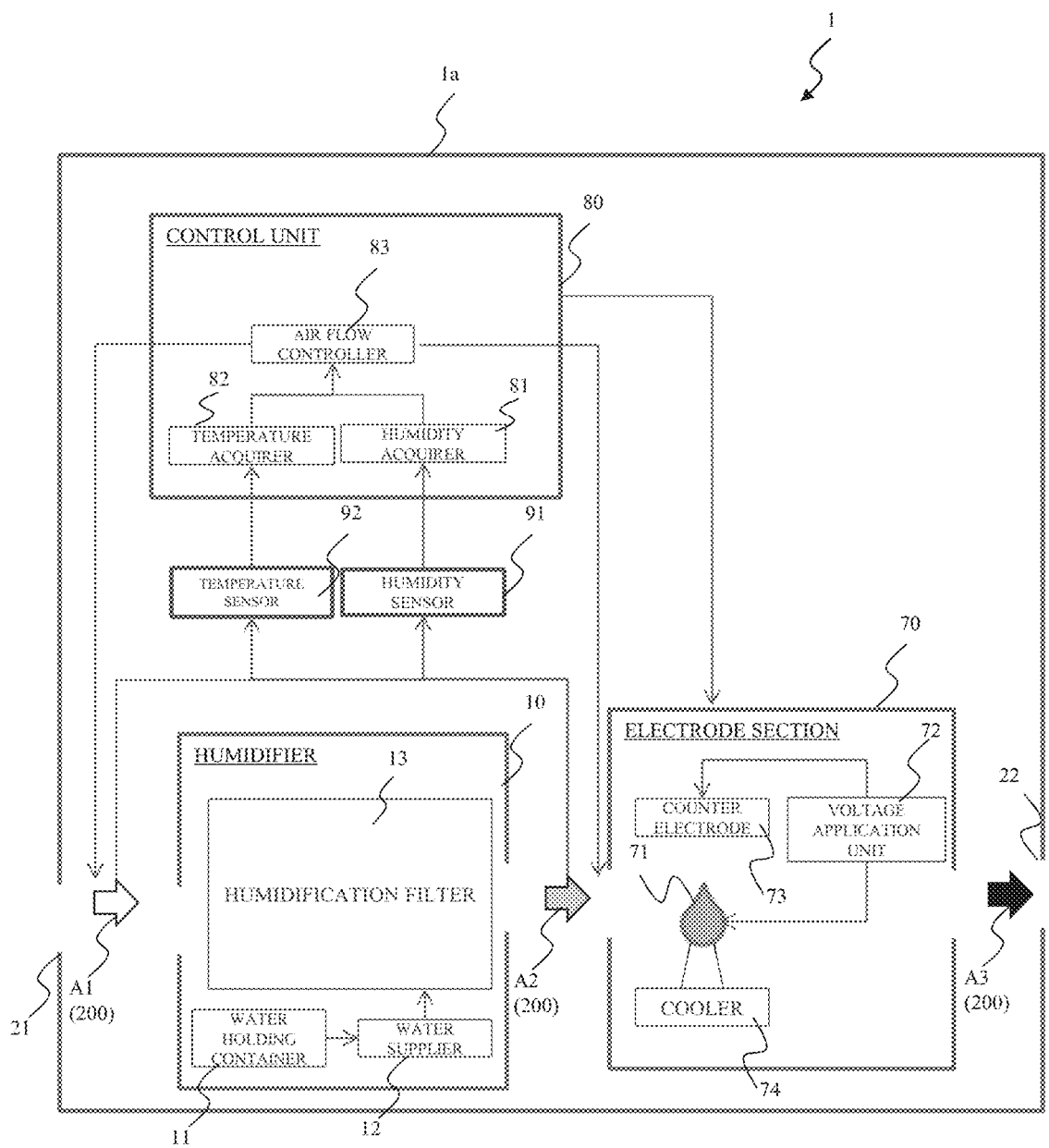

FIG. 1 is a block diagram illustrating the schematic configuration of an electrostatic atomizing apparatus 1 that is installed in an aircraft.

The electrostatic atomizing apparatus 1 can be installed in the aircraft near a seat (front surface of the seat, rear surface of the seat, side surface of the seat, under the seat, in the armrest, or the like), near the aisle (under the floor, in the ceiling, or the like), near the galley, near the lavatory, in a moving body (meal trolley, trash collection trolley, or the like), or the like.

As illustrated in FIG. 1, the electrostatic atomizing apparatus 1 includes a main body portion 1*a*, and a control unit 80, a humidifier 10, and an electrode section 70 that are disposed in the main body portion 1*a*. Note that the control unit 80, the humidifier 10, and the electrode section 70 need not be integrally formed in the main body portion 1*a* of the electrostatic atomizing apparatus 1. That is, these constituents may be appropriately separated and disposed. For example, the control unit 80 and the humidifier 10 may be configured as a first unit, and the electrode section 70 may be configured as a second unit.

The main body portion 1*a* includes an air intake port 21 and an air exhaust port 22. An air flow path 200 is formed from the air intake port 21 to the air exhaust port 22. The air flow path 200 consists of the flows of air A1, A2, and A3. The air A1 is unhumidified air. The air A2 is humidified air. The air A3 is post-electrostatic atomization air that contains charged particulate water.

The humidifier 10 includes a portion of the air flow path 200. The humidifier 10 includes a water holding container 11, a water supplier 12, and a humidification filter 13.

The water holding container 11 is implemented as a container that has a tank shape or a tray shape to hold water. The water holding container 11 is detachably attached to the main body portion 1*a*. A user can detach the container in order to replenish the water. The humidification filter 13 is formed from paper or resin that contains water. The humidified air A2 is produced as a result of the unhumidified air A1 passing through the humidification filter 13. The water in the water holding container 11 is fed to the humidification filter 13 by the water supplier 12. The water fed to the humidification filter 13 vaporizes based on the flow of the air. As a result, the air is humidified. Note that a configuration is feasible in which the water supplier 12 is not provided and the water is fed directly to the humidification filter 13 from the water holding container 11.

Additionally, a configuration is feasible in which the entire humidifier 10, including the water holding container 11, the water supplier 12, and the humidification filter 13, are replaceable. Moreover, a configuration is feasible in which only the humidification filter 13 or only the water holding container 11 is replaceable.

In the humidifier 10, water is only replenished and vaporized and there is no risk of damage or deterioration. However, mold or the like may grow, thereby negatively affecting the hygienic characteristics of the humidifier 10. Additionally, since the water vaporizes continually and the air is humidified, the mineral components contained in the water may crystallize and occur clogging. Maintenance should be regularly or irregularly required to replace the humidifier 10 in order to avoid such worsening of the hygienic characteristics and clogging. Moreover, in cases in which the water in the water holding container 11 is insufficient, a jug, dropper, or the like may be used to directly add water to the water holding container 11. Alternatively, in a case in which the water holding container 11 is detachable and the water holding container 11 is empty, water may be added by completely detaching the water holding container 11 and attaching a different water holding container 11. That is, the water holding container 11 is replaced.

The electrode section 70 includes a water application electrode 71, a voltage application unit 72, a counter electrode 73, and a cooler 74. Upon receipt of a command from the control unit 80, the cooler 74 cools the water application electrode 71. As a result of this cooling, the water vapor in the air A2 is liquefied and caused to condense on the water application electrode 71. Upon receipt of a command from the control unit 80, the voltage application unit 72 applies high voltage between the counter electrode 73 and the water application electrode 71. The cooler 74 may be implemented as a device such as a Peltier element that cools by electrical control, a device that cools by a heat pump mechanism such as a compressor, or may be implemented as another device or method.

High voltage is applied to the counter electrode 73 and the water application electrode 71 that is cooled and on which condensation has occurred. As a result, the condensation water on the water application electrode 71 is pulled to the counter electrode 73, charged negatively by the water application electrode 71, and split. As a result, charged particulate water is spread into the air A2, thereby producing the air A3. Since air ionization using the electrode section 70 is a well-known technique (see Japanese Patent No. 4877410, for example), detailed description thereof is foregone.

The electrostatic atomizing apparatus 1 can inactivate any of pollen antigens, molds, fungi, and viruses, and can enhance odor prevention and moisturization. Only a small amount of water is required to realize the capabilities of the electrostatic atomizing apparatus 1. An appropriate amount of water can be efficiently supplied on the surface of the water application electrode 71 by causing the water in the air to condense and collecting that water. Note that, a method is conceivable in which the water holding container 11 of the humidifier 10 is connected to the surface of the water application electrode 71 by a fibrous string and the water in the water holding container 11 is transferred to the surface of the water application electrode 71 by surface tension. However, with such a method, the amount of water is difficult to regulate, the discharge area is difficult to control, and practical use will be extremely difficult. Meanwhile, the method in which water is acquired by cooling and condensing is thought to be a practical method.

One or a plurality of microcomputers/microcontrollers realizes the control unit 80. In such a case, the microcomputer/microcontroller includes a processor that includes a circuit such as a CPU, and a storage unit such as ROM, flash memory, RAM, or the like. Using the RAM as workspace, the processor executes a computer program stored in the ROM to realize the functions of the various components of the electrostatic atomizing apparatus 1 such as, for example, a humidity acquirer 81, a temperature acquirer 82, and an air flow controller 83. The humidity acquirer 81 acquires humidity measured with a humidity sensor 91. The temperature acquirer 82 acquires a value of a temperature sensed with a temperature sensor 92. The air flow controller 83 controls, in accordance with the humidity or the temperature acquired by the humidity acquirer 81 or the temperature acquirer 82, a blower 50 (described later) that is disposed in the air flow path 200, thereby regulating the flow rate of the air in the air flow path 200. In addition, the control unit 80 controls the operations of the cooler 74 and the voltage application unit 72 of the electrode section 70.

The electrostatic atomizing apparatus 1 further includes a humidity sensor 91 and a temperature sensor 92. The humidity sensor 91 senses the humidity in the air flow path 200 and sends the sensed data to the control unit 80. The temperature sensor 92 senses the temperature in the air flow path 200 and sends the measured data to the control unit 80. The humidity sensor 91 senses the humidity of the air A1 before flowing into the humidifier 10 and/or the humidity of the air A2 that flows out of the humidifier 10. The temperature sensor 92 senses the temperature of the air A1 before flowing into the humidifier 10 and/or the temperature of the air A2 that flows out of the humidifier 10.

Three main factors determine the amount of humidification to the air. The first factor is the shape and surface area of the humidification filter 13. The second factor is the temperature and humidity of the air that is introduced. The third factor is the flow rate of the air. It is not realistic to change the shape and the surface area of the humidification filter 13 depending on the situation. Moreover, since the temperature and the humidity of the air that is introduced are external factors, they are not subject to change. Therefore, the electrostatic atomizing apparatus 1 of the present disclosure regulates the flow rate of the air according to the temperature or the humidity of the introduced air so that the humidity becomes higher than the required after humidification.

Figure 10:
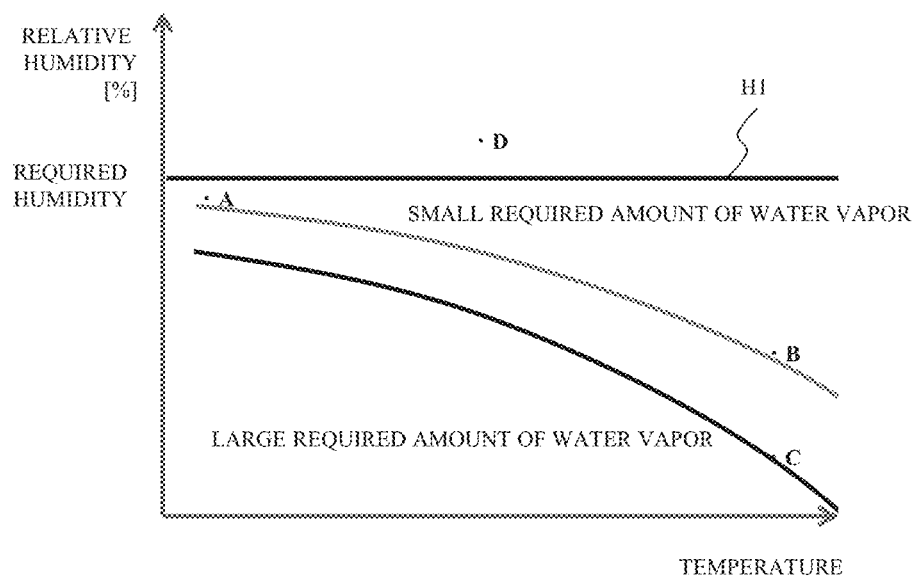

FIG. 10 illustrates a graph for explaining the required amount of water vapor for the electrostatic atomizing apparatus 1. In this graph, the curves represent absolute humidity. The curves depict that humidification of the same amount of water vapor is required for the target required humidity H1. For example, humidification of the same amount of water vapor is required at point A and at point B. In cases of high temperature/low humidity such as at point C, the required amount of water vapor increases. Meanwhile, in cases of low temperature/high humidity such as at point A, the required amount of water vapor decreases. Additionally, in cases above the required humidity H1 such as at point D, humidification is not necessary.

The maximum amount of humidification is dependent on the flow rate of the air. If the flow rate of the air to the humidification filter 13 decreases, the maximum amount of humidification per unit volume of the air increases. The humidification can be controlled by regulating the flow rate of the air to the humidification filter 13 in accordance with the temperature and/or the humidity of the introduced air.

In Embodiment 1, one or a plurality of blowers 50 (FIGS. 2 and 3) are disposed on the air flow path 200, and the one or plurality of blowers 50 is controlled by the control unit 80. As a result, the flow rate of the air in the air flow path 200 is regulated.

Figure 2:
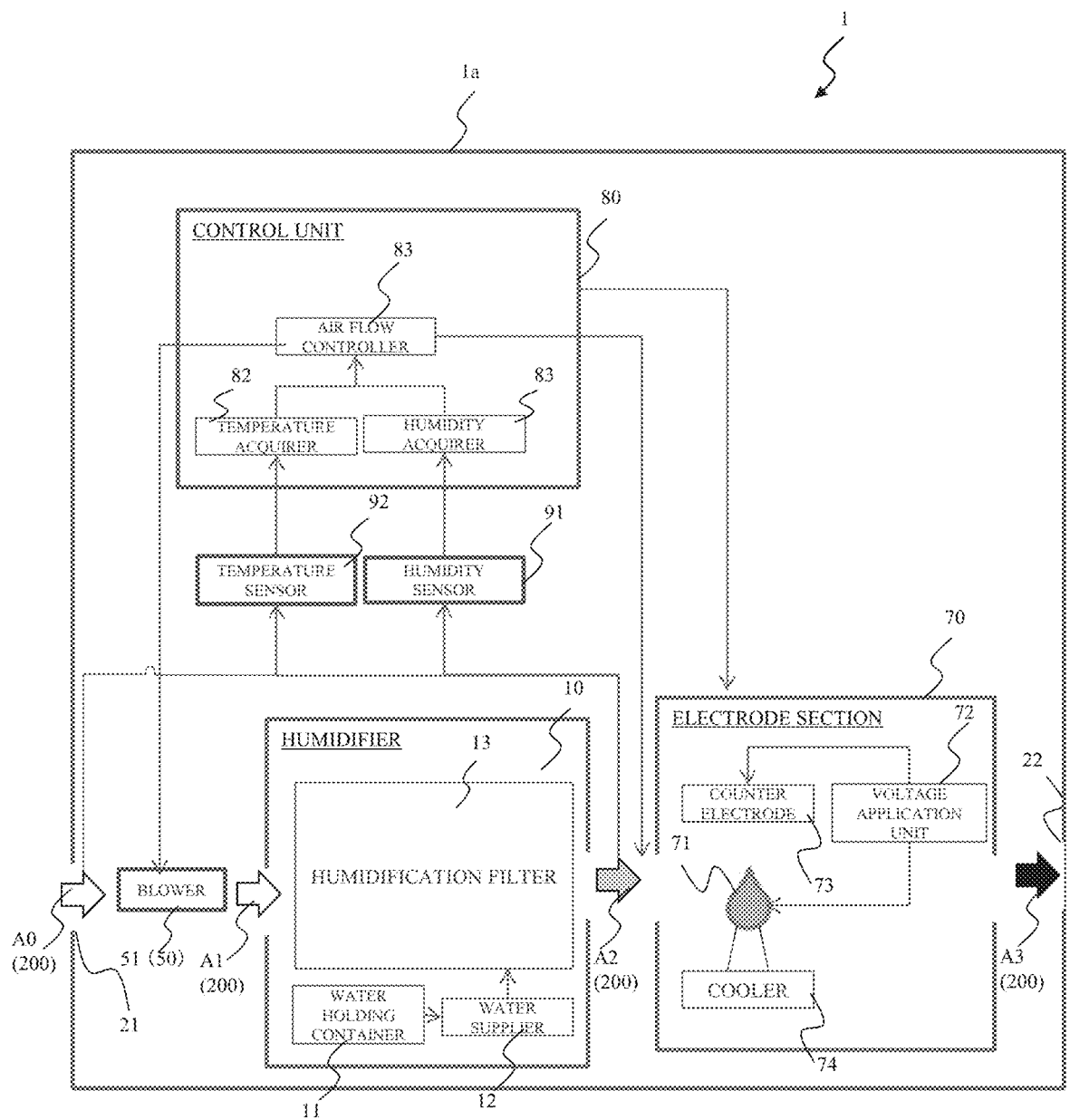

FIG. 2 is a configuration example of the electrostatic atomizing apparatus 1 according to Embodiment 1. As illustrated in FIG. 2, the blower 51 is disposed in the air flow path 200, upstream from the humidifier 10. In one example, the blower 51 is a fan. The ON/OFF operations and the rotation speed of the blower 51 are controlled by the air flow controller 83.

Figure 3:
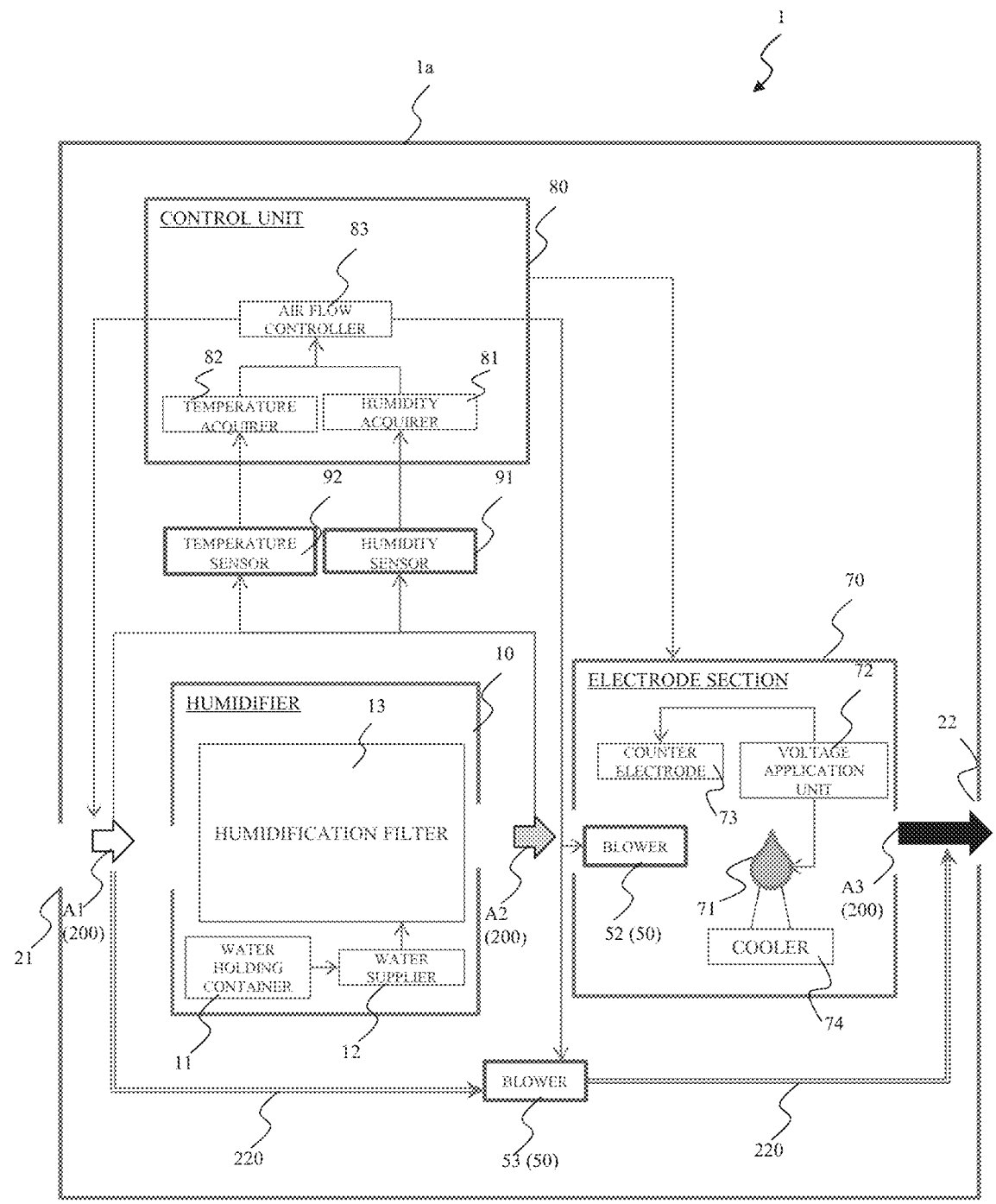

FIG. 3 is a modification example of the electrostatic atomizing apparatus 1 according to Embodiment 1. As illustrated in FIG. 3, a blower 52 is disposed on the air flow path 200 in the electrode section 70. Furthermore, the electrostatic atomizing apparatus 1 forms a second air flow path 220 that does not pass through the humidifier 10 and the electrode section 70, and another blower 53 is disposed on this air flow path 220. In one example, the blowers 52 and 53 are fans. The air flow controller 83 controls the ON/OFF operations and the rotation speeds of the blowers 52 and 53.

Note that the number and positions of the blowers in FIGS. 2 and 3 are given as examples and are not limited thereto. For example, another blower may be disposed between the humidifier 10 and the electrode section 70 in addition to or in place of the blower 51 (FIG. 2). Alternatively, only the blower 52 in the electrode section 70 may be disposed.

1-2 Operations 1-2-1 Humidification

Figure 4:
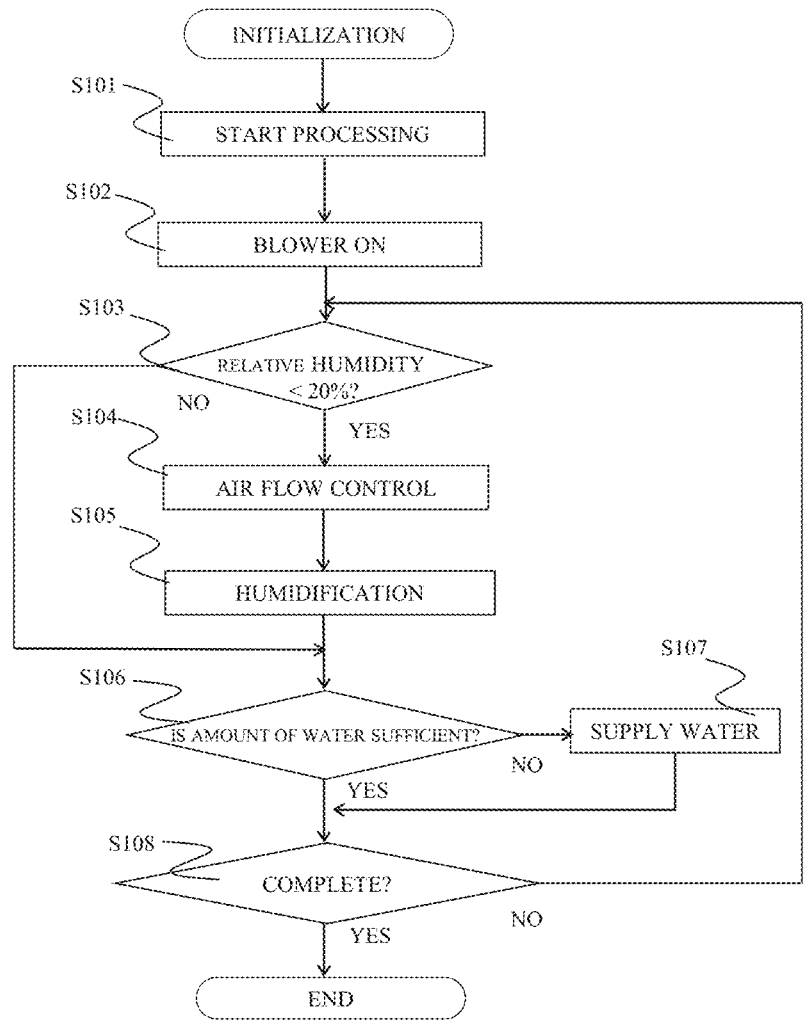

Next, FIG. 4 explains the operations of air humidification executed in the electrostatic atomizing apparatus 1. The power turns ON and the electrostatic atomizing apparatus 1 starts (step S101). When the start processing is completed, the control unit 80 sends a command to the blower 50 and turns the blower 50 ON (step S102). A flow of air is generated in the air flow path 200 by the operations of the blower 50. As a result, outside air is taken in through the air intake port 21 and air is exhausted through the air exhaust port 22.

Next, the humidity sensor 91 measures the humidity in the air flow path 200, and the humidity acquirer 81 acquires the sensed humidity. The air flow controller 83 determines whether the humidity from the humidity acquirer 81 is a predetermined value such as, for example, less than 20%. When the humidity is less than 20%, the air flow controller 83 determines that humidification is insufficient. When the humidity is 20% or greater, the air flow controller 83 determines that humidification is sufficient (step S103). When the humidity of the air in the air flow path 200 is sufficient (step S103; No), step S106 is executed. Note that, at this time, in cases in which the blower 50 is OFF or the rotation speed is slow, the control unit 80 may control the blower 50 so as to turn the blower 50 ON or speed up the rotation.

When the humidity of the air in the air flow path 200 is insufficient (step S103; Yes), step S104 is executed. Specifically, the air flow controller 83 sends a command to the blower 50 and controls the blower 50 (step S104). The phrase "control the blower 50" means, for example, to turn the blower 50 OFF, slow down the rotation of the fan, or the like. As a result, the flow of the air in the air flow path 200 weakens and, as such, the amount of water vapor from the humidification filter 13 increases and the humidification of the air flow path 200 is promoted (step S105).

A crew member confirms the amount of water in the water holding container 11. When the amount of water is insufficient, water is supplied by replacing an empty cartridge with a cartridge containing water, or injecting water into the water holding container 11 using a dropper or the like (step S107). Note that, when the amount of water is insufficient, a display or a sound alert may be output from an output unit (not illustrated in the drawings) located on the electrostatic atomizing apparatus 1. Alternatively, a notification that the amount of water is insufficient may be issued, by a communication unit (not illustrated in the drawings), via an external device other than the electrostatic atomizing apparatus 1. For example, a host system (not illustrated in the drawings) installed in the aircraft notifies the insufficiency of water.

In step S108, a determination is made on whether the air humidification is enough. When it is determined that the air humidification is enough, the operations of the electrostatic atomizing apparatus 1 end. Meanwhile, when it is determined that the air humidification is not enough, step S103 is executed and the blowing control described above is continued. For example, in a case in which the electrostatic atomizing apparatus 1 of the present disclosure is installed in an aircraft, the operations of the electrostatic atomizing apparatus 1 may be ended by automatically turning OFF the power source of the electrostatic atomizing apparatus 1 at the timing when a change occurs in the flight phase (take off, cruising, landing, or the like), the cabin situation (whether meal service is provided, whether lavatories are in use), or the altitude (at an altitude of 10 km, on the ground, or the like) of the aircraft.

When there is a plurality of blowers 50, the control in step S104 is not limited to controlling all of the blowers 50, and a portion of the plurality of blowers 50 may be controlled. For example, the blower for which blowing is to be controlled may be only the blower upstream from the humidifier 10 (for example, blower 51 in FIG. 2). Additionally, a portion of the plurality of blowers 50 may be turned OFF, and the rotation of the fans of another portion of the plurality of blowers 50 may be slowed down.

In Embodiment 1, the blower 50 may be controlled in accordance with the temperature of the air. For example, in cases in which the temperature measured by the temperature sensor 92 is 30° C. or higher, the control unit 80 may turn the blower 50 OFF or slow down the rotation of the fan in order to further promote the humidification per unit volume of the air to be humidified by the humidifier 10.

In Embodiment 1, the blower 50 may be controlled in accordance with the humidity and the temperature. In this case, when, for example, the humidity is less than 20% or the temperature is 30° C. or higher, a command may be issued to each blower 50 to turn that blower 50 OFF or slow down the rotation of the fan of that blower 50.

In Embodiment 1, after step S105, when, for example, it is determined on the basis of the measured humidity or temperature that the humidity required for electrostatic atomization has been restored, control may be carried out to turn the blower 50 back ON, speed up the rotation, or the like.

In Embodiment 1, the blower 50 turns ON in step S102 after the start processing, but the present disclosure is not limited thereto. Control is possible in which the blower 50 is set to OFF and, in cases in which it is determined that the humidity is sufficient in step S103, the blower 50 turns ON.

1-2-2 Electrostatic Atomization

Figure 5:
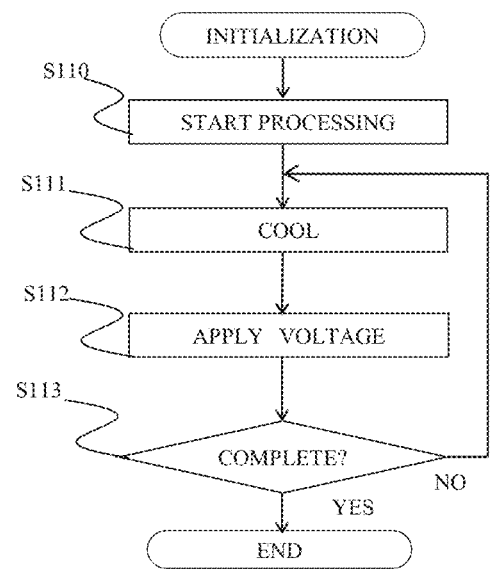

Next, FIG. 5 explains the operations of electrostatic atomization of the electrostatic atomizing apparatus 1.

The power turns ON and the electrostatic atomizing apparatus 1 starts (step S110). Note that initialization is the same as the initialization of FIG. 4, and the start of the electrostatic atomizing apparatus 1 is the same as the start of FIG. 4. Additionally, the following operations are typically executed simultaneously with the operations of FIG. 4.

Upon completion of the start processing, the control unit 80 sends a command to the cooler 74 and cools the water application electrode 71 (step S111). As a result of the cooling, water condensation from the air adheres to the surface of the water application electrode 71.

Next, the control unit 80 sends a command to the voltage application unit 72, and the voltage application unit 80 applies high voltage between the counter electrode 73 and the water application electrode 71 (step S112). Discharge occurs as a result of the application. Due to this discharge, the water adhered to the surface of the water application electrode 71 is spread into the air as charged particulate water. The control unit 80 determines whether the processing flow of the electrostatic atomization is completed (S113). When it is determined that the processing flow of the electrostatic atomization is completed, the operations of the electrostatic atomizing apparatus 1 end. Meanwhile, when it is determined that the processing flow is not completed, step S111 is executed. The end of these operations are the same as the end of the operations of FIG. 4.

1-3 Features and the Like

The electrostatic atomizing apparatus 1 or the electrostatic atomizing method according to Embodiment 1 regulates the flow rate of the air in accordance with the humidity or the temperature of the introduced air. Due to this, humidification water can be supplied to the humidification filter 13 and the humidification of the air to be sent to the water application electrode 71 can be controlled. As a result, electrode cooling-type electrostatic atomization can be stably carried out in low humidity environments such as in aircraft, and the advantageous benefits of inactivating pollen antigens, molds, fungi, viruses, and the like can be demonstrated to the greatest extent possible.

Additionally, the required humidity can be realized while supplying the minimal amount of water to the humidification filter 13.

2. Embodiment 2

An electrostatic atomizing apparatus according to Embodiment 2 controls the humidification of the air sent to the electrode section 70 by providing a control mechanism that opens and closes the air flow path. The following of the electrostatic atomizing apparatus 201 according to Embodiment 2 describes the differences from the electrostatic atomizing apparatus 1 of Embodiment 1. Note that constituents and functions that are the same as in Embodiment 1 are marked with the same reference numerals and detailed descriptions thereof are foregone.

2-1 Configuration

Figure 6:
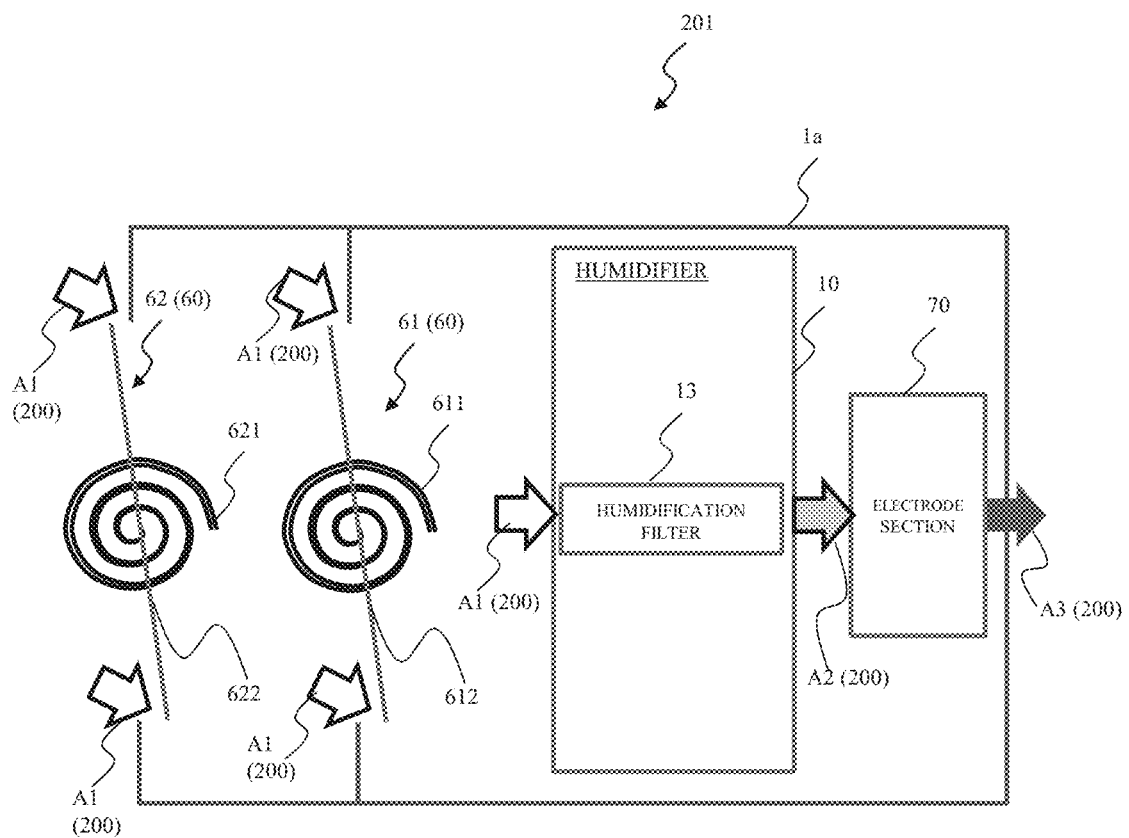
Figure 7:
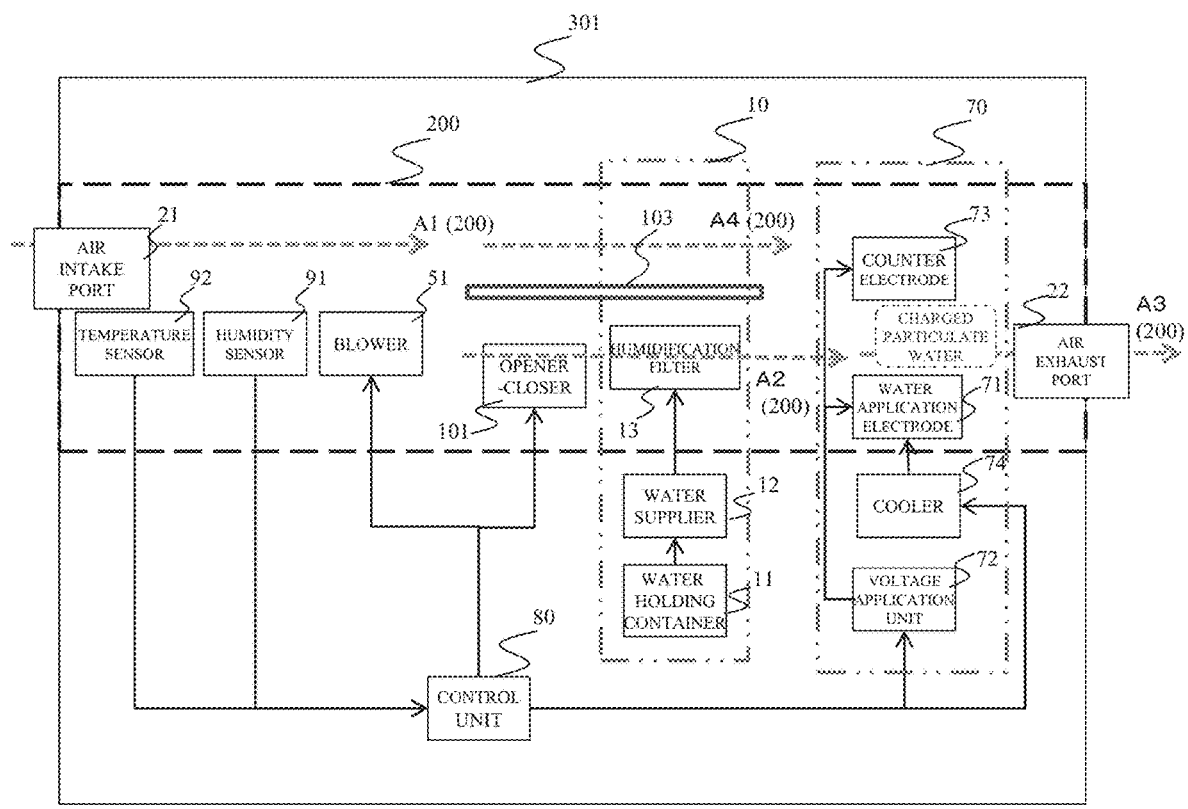
Figure 8:
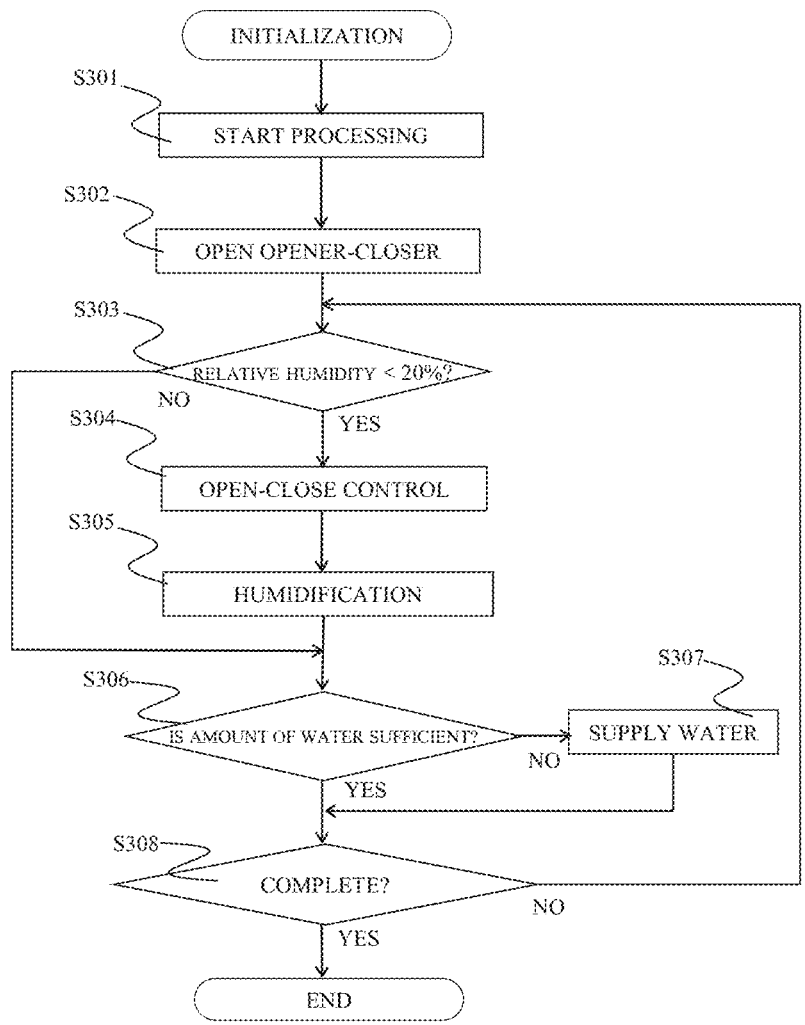
Figure 9:
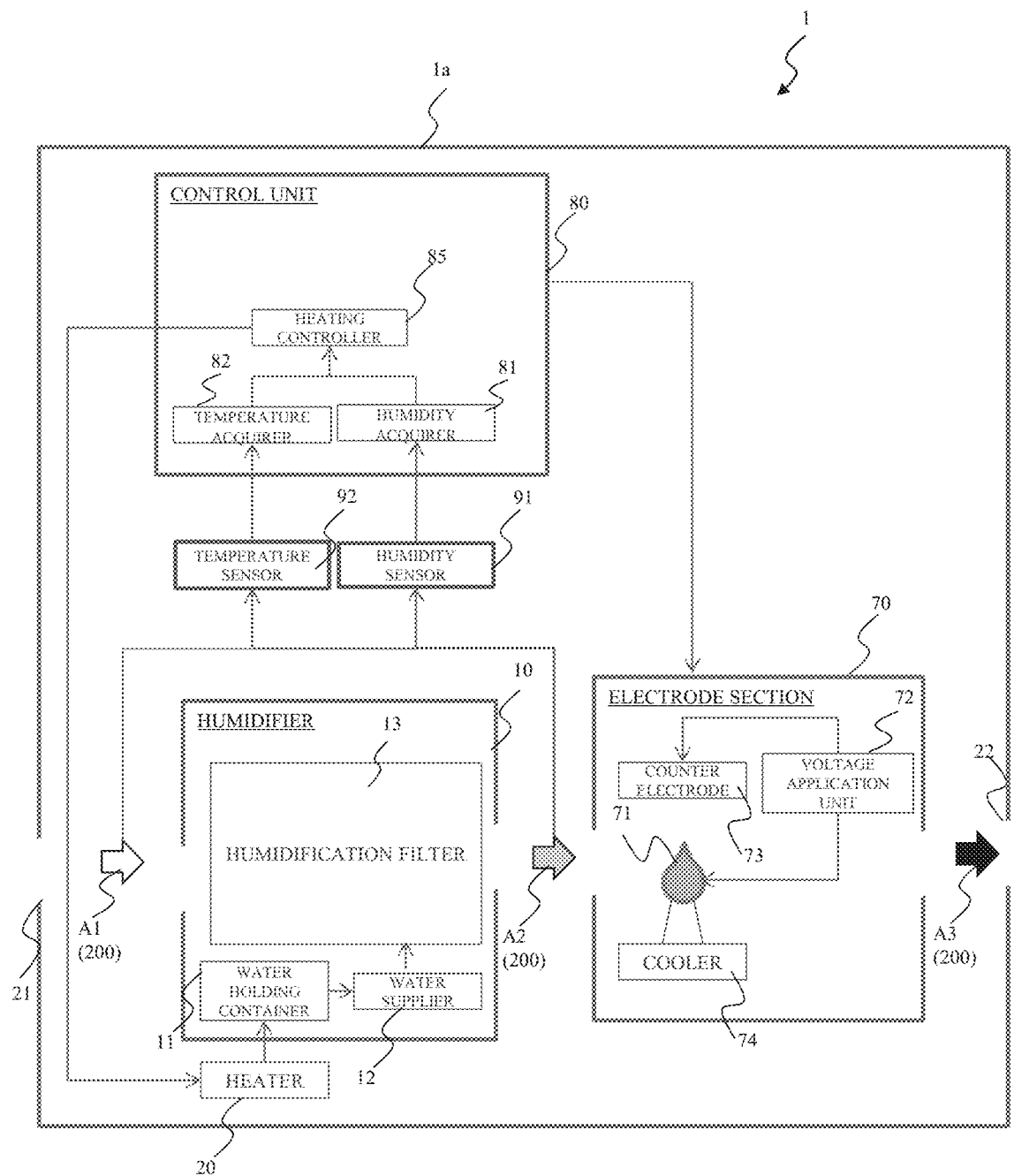

FIG. 6 is a drawing that illustrates an example of open-close rate control, based on temperature and humidity, of the electrostatic atomizing apparatus 201. A control unit 60 of the electrostatic atomizing apparatus 201 includes a humidity-based open-close rate controller 61, and a temperature-based open-close rate controller 62. The open-close rate controller 61 and the open-close rate controller 62, which are examples of the control unit, are disposed upstream from the humidifier 10 in the air flow path 200.

The humidity-based open-close rate controller 61 and the temperature-based open-close rate controller 62 respectively include spiral-shape substances 611 and 621. These two types of spiral-shape substances 611 and 621 have different coefficients of thermal expansion and different humidity-sensitive characteristics. The center portions of the spirals are fixed to doors 612 and 622 (examples of the open-close mechanism), and the ends of the spirals are fixed to portions of the main body portion 1*a*.

In one example, the substance 611 is obtained by adhering a material that expands and contracts due to changes in humidity (example of the humidity-sensitive material) to a thin sheet of metal (example of the non-humidity-sensitive material) and winding in a spiral shape. With the substance 611, the humidity-sensitive material expands and contracts due to changes in humidity but the metal does not expand and contract. As such, the open-close rate of the door 612 changes in accordance with the winding and returning of the spiral.

The substance 621 is formed by adhering two metal layers with different coefficients of thermal expansion, and winding in a spiral shape. With the substance 621, the layer with the larger coefficient of thermal expansion expands and contracts more due to changes in temperature, and the open-close rate of the door 622 changes in accordance with the winding and returning of the spiral.

Due to the configuration described above, the open-close rates of the doors change in accordance with the temperature and the humidity, and the flow rate of the air flowing into the humidifier 10 can be changed.

Note that FIG. 6 merely illustrates an example, and the two types of substances may have linear shapes instead of spiral shapes. Additionally, one door may be disposed instead of two doors. Moreover, the open-close direction of the doors according to the temperature and the humidity may be different. For example, the open-close directions may be set to be vertical, horizontal, or the like.

The humidity-based open-close rate controller 61 and/or the temperature-based open-close rate controller 62 may perform open-close control of the doors 612 and 622 using a humidity sensor and/or a temperature sensor.

2-2 Operations

When the humidity goes down, the spiral of the substance 611 changes in the returning direction and the door 612 is moved in the closing direction. When the humidity goes up, the spiral of the substance 611 changes in the winding direction and the door 612 is moved into the opening direction. When the door 612 moves into the opening direction, the flow rate of the air strengthens. When the door 612 moves into the closing direction, the flow rate of the air weakens.

When the temperature rises, the spiral of the substance 621 changes in the returning direction and the door 622 is moved into the closing direction. When the temperature decreases, the spiral of the substance 621 changes in the winding direction and the door 622 is moved into the opening direction. When the door 622 moves icon the opening direction, the flow rate of air strengthens. When the door 622 moves into the closing direction, the flow rate of air weakens.

2-3 Features and the Like

The electrostatic atomizing apparatus 201 or the electrostatic atomizing method according to Embodiment 2 controls the open-close rate of the air flow path 200 in accordance with the temperature or the humidity. By linking the expansion and contraction of the metal in the open-close rate controllers 61 and 62 to the opening and closing of the air flow path 200, the flow rate of the air flowing into the humidification filter 13 can be regulated. As a result, electrode cooling-type electrostatic atomization can be stably carried out in low humidity environments such as in aircraft, and the benefits of inactivating pollen antigens, molds, fungi, viruses, and the like can be demonstrated to the greatest extent possible. Additionally, the required humidity can be realized while supplying the minimal amount of water to the humidification filter 13.

3. Embodiment 3

The following description of the electrostatic atomizing apparatus 301 according to Embodiment 3 focuses on the differences from the electrostatic atomizing apparatus 1 of Embodiment 1. Note that constituents and functions that are the same as in Embodiment 1 are marked with the same reference numerals and detailed descriptions thereof are foregone.

3-1 Configuration

FIG. 7 is a block diagram that illustrates the configuration of an electrostatic atomizing apparatus 301 according to Embodiment 3. The electrostatic atomizing apparatus 301 includes an inner wall 103 and an opener-closer 101 that is controlled by the control unit 80. The inner wall 103 has a structure that divides the air flow path 200 into a path that passes through the humidifier 10 and the other path that does not pass through the humidifier 10. The opener-closer 101 includes a mechanism (for example, a lid, a valve, or the like) that opens and closes the air flow path 200. The inner wall 103 and the opener-closer 101 are disposed upstream of the electrode section 70 in the air flow path 200, and near the humidifier 10.

The air flow path 200 that is divided by the inner wall 103 includes an air flow path in which the humidified air A2 flows, and the other air flow path in which air A4, which does not pass through the humidifier 10 and is not humidified, flows.

The opener-closer 101 is disposed in the air flow path 200 at the portion where the inner wall 103 is present, and is controlled by the control unit 80. The opener-closer 101 may open and close only one of the air flow paths 200 (the humidification filter 13 side) divided by the inner wall 103. Alternatively, a configuration is feasible in which the opener-closer 101 is disposed in the one air flow path 200 and the other air flow path 200 that are divided by the inner wall 103, and be reverse controlled so as to open the other air flow path 200 and close the one air flow path 200. When reverse controlling the opener-closer 101, of the air flow paths 200 divided by the inner wall 103, the air flows only on the humidifier 10 side or only on the opposite side. In this case, the flow rate of the air does not change, but whether the humidity of the air flowing to the electrode section 70 is increased or decreased can be switched by opening or closing the humidification filter 13 side.

The humidified air A2 or the unhumidified air A4 that has passed through the opener-closer 101 and the inner wall 103 is introduced into the electrode section 70. As in Embodiment 1, in the electrode section 70, charged particulate water is spread into the air flow path 200 and electrostatic atomization is performed.

Note that, a configuration is feasible in which, in addition to or in place of the example illustrated in FIG. 7, the opener-closer 101 is disposed at the air intake port 21 or the air exhaust port 22 on the air flow path 200. In this case, the air intake port 21 or the air exhaust port 22 is opened and closed by the opener-closer 101, in accordance with control by the control unit 80.

3-2 Operations

FIG. 8 illustrates a flowchart of the operations of humidification executed in the electrostatic atomizing apparatus 301. Step S301 is the same as step S101 (FIG. 4) in Embodiment 1. In step S302, the opener-closer 101 opens.

In step S303, when the humidity in the air flow path 200 is insufficient such as when, for example, the humidity is less than 20% (step S303; Yes), step S304 is executed. Specifically, the control unit 80 sends a command to the opener-closer 101 disposed on the air flow path 200 of the humidifier 10, and closes the air flow path 200 (S304). As a result, the flow in the air flow path 200 weakens and, as such, the amount of humidification per unit volume of the air to be humidified from the humidification filter 13 can be increased, and the humidification of the air flow path 200 is promoted (step S305). Meanwhile, in step S303, when the humidity of the air in the air flow path 200 is sufficient (step S303; No), step S306 is executed. Note that, at this time, in cases in which the opener-closer 101 is closed, the control unit 80 may open the opener-closer 101.

Steps S306 to S308 are the same as steps S106 to S108 (FIG. 4) in Embodiment 1.

In Embodiment 3, the open-close control of the opener-closer 101 may be carried out in accordance with the temperature of the air. For example, in cases in which the temperature measured by the temperature sensor 92 is 30° C. or higher, the control unit 80 may issue a command to the opener-closer 101 and close the air flow path 200 in order to further promote humidification.

In Embodiment 3, the open-close control of the opener-closer 101 may be performed in accordance with the humidity and the temperature. In this case, when, for example, the humidity is less than 20% or the temperature is 30° C. or higher, a command may be issued to opener-closer 101 to close the air flow path 200.

In Embodiment 3, after step S305, when, for example, it is determined on the basis of the measured humidity or temperature that the humidity required for electrostatic atomization has been restored, the opener-closer 101 may be reopened.

In Embodiment 3, the opener-closer 101 is opened in step S302 after the start processing, but the present disclosure is not limited thereto. Control is possible in which the opener-closer 101 is set as closed and, in cases in which it is determined that the humidity is sufficient in step S303, the opener-closer 101 is opened.

3-3 Features and the Like

The electrostatic atomizing apparatus 301 or the electrostatic atomizing method according to Embodiment 3 regulates the flow rate of the air in accordance with the humidity or the temperature of the introduced air by opening and closing the opener-closer 101. This configuration enables the water application electrode 71 to control the humidification of the air to be sent to the electrode. As a result, electrode cooling-type electrostatic atomization can be stably carried out in low humidity environments such as in aircraft, and the benefits of inactivating pollen antigens, molds, fungi, viruses, and the like can be demonstrated to the greatest extent possible.

Additionally, the required humidity can be realized while supplying the minimal amount of water to the humidification filter 13.

4. Other Embodiments

In Embodiments 1 and 3, examples were given in which one threshold was set for each of the humidity and temperature that regulates the flow rate of the air. However, a configuration is feasible in which pluralities of thresholds are used. For example, for the humidity, control may be executed in which the flow rate of the air is weakens when the humidity is less than 25% and set to zero when the humidity is less than 20%. For example, for the temperature, control may be executed in which the flow rate of the air is weakens when the temperature is 25° C. or higher and set to zero when the temperature is less than 30° C. or higher. Moreover, for the humidity and the temperature, limit thresholds for the stable execution of electrostatic atomization may be set, and the control unit 80 may stop the operation of the electrostatic atomizing apparatus 1 if the limit thresholds are not reached.

In Embodiments 1 to 3, as illustrated in FIG. 9, the electrostatic atomizing apparatuses 1, 201, and 301 may also include a heating unit 20, such as a heater, that heats the water in the water holding container 11 of the humidifier 10. By heating the water in the water holding container 11, the amount of water vapor in the air flow path 200 can be increased and humidification can be promoted. In this case, the control unit 80 that includes the processor executes the functions of a heating controller 85 on the basis of the sensed humidity or temperature. When the heating controller 85 determines, on the basis of the humidity or the temperature, that the humidification is insufficient, the heating controller 85 causes the heating unit 20 to operate and heat the water in the water holding container 11.

In Embodiments 1 to 3, examples are described that focus on an aircraft as the space in which the electrostatic atomizing apparatuses 1, 201, and 301 are used, but the space in which the electrostatic atomizing apparatuses 1, 201, and 301 are used is not limited thereto. The electrostatic atomizing apparatuses 1, 201, and 301 may be installed in a train, a bus, a marine vessel, or other vehicle, or in a facility located in a low humidity environment.

General Interpretation of Terms

In understanding the scope of the present disclosure, the term "configured" as used herein to describe a component, section, or a part of a device includes hardware and/or software that is constructed and/or programmed to carry out the desired function.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including," "having," and their derivatives. Also, the terms "part," "section," "portion," "member," or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of a device.

Terms that are expressed as "means-plus function" in the claims should include any structure that can be utilized to carry out the function of that part of the present disclosure. Finally, terms of degree such as "substantially," "about," and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected exemplary embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the exemplary embodiments according to the present invention are provided for illustration only, and not for the purpose of limiting the invention as defined by the appended claims and their equivalents.

What is claimed:

1. An electrostatic atomizing apparatus, comprising:
   an air flow path having an air intake port and an air exhaust port;
   a humidifier including a first portion of the air flow path and operable to humidify air in the air flow path;
   an electrode section including a second portion of the air flow path and operable to produce charged particulate water by causing water in the air humidified by the humidifier to condense on an electrode and applying voltage to the electrode;
   a blower operable to increase a flow rate of the air in the air flow path; and
   a control unit including a processor that detects the humidity of the air in the air flow path and operable to change a drive state of the blower in accordance with the humidity;
   wherein:
   the blower includes a fan,
   the control unit is operable to change the drive state of the blower by turning the fan ON or OFF, or changing a rotation speed of the fan, and
   when the humidity is less than a first predetermined value, the control unit turns the fan OFF or slows down the rotation of the fan reducing the flow rate of the air humidified by the humidifier and introduced into the electrode section.

2. The electrostatic atomizing apparatus according to claim 1, wherein
   the blower is disposed on at least one of upstream of the humidifier in the air flow path and downstream of the humidifier in the air flow path.

3. The electrostatic atomizing apparatus according to claim 1, wherein the blower includes a first blower disposed in the electrode section, and a second blower disposed downstream of the humidifier in the air flow path.

4. The electrostatic atomizing apparatus according to claim 1, wherein:
   the processor detects the temperature of the air in the air flow path and is operable to change the drive state of the blower in accordance with the temperature;
   wherein:
   when the temperature is higher than or equal to a second predetermined value, the control unit turns the fan OFF or slows down the rotation of the fan.

5. The electrostatic atomizing apparatus according to claim 1, wherein:
   the control unit includes an open-close mechanism that opens and closes the air flow path, and
   the open-close mechanism is capable of changing an open-close rate of the air flow path in accordance with the humidity.

6. The electrostatic atomizing apparatus according to claim 5, wherein:
   the control unit includes bimetals that have different coefficients of thermal expansion, and
   the open-close mechanism is capable of changing the open-close rate of the air flow path by contraction or expansion of the bimetals.

7. The electrostatic atomizing apparatus according to claim 5, wherein:
   the control unit includes a humidity-sensitive material and a non-humidity-sensitive material, and
   the open-close mechanism is connected to the control unit and is capable of opening and closing the air flow path by contraction or expansion of the humidity-sensitive material.

8. The electrostatic atomizing apparatus according to claim 1, wherein:
   the control unit includes a processor that senses the temperature of the air in the air flow path,
   the electrostatic atomizing apparatus further includes an opener-closer configured to open and close the air flow path, and
   the control unit is operable to control opening and closing of the opener-closer in accordance with at least one of the humidity and the temperature.

9. The electrostatic atomizing apparatus according to claim 1, further comprising:
   a structure that divides the air flow path into an air flow path that passes through the humidifier and an air flow path that does not pass through the humidifier.

10. The electrostatic atomizing apparatus according to claim 1, wherein:
    the humidifier includes a container configured to hold water,
    the electrostatic atomizing apparatus further includes a heater that is controlled by the control unit and operable to heat the water in the container, wherein
    when the humidity is a first predetermined value or lower, the control unit heats the water in the container using the heater.

* * * * *